(12) United States Patent
Borut et al.

(10) Patent No.: US 6,389,739 B1
(45) Date of Patent: May 21, 2002

(54) ADJUSTABLE BURNABLE COIL CONTAINER

(75) Inventors: Adam K. Borut, Milwaukee; Brian T. Davis, Racine; Therese M. Nelson, Racine; Allen D. Miller, Racine, all of WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/619,228

(22) Filed: Jul. 19, 2000

(51) Int. Cl.[7] ............................................. A01M 13/00
(52) U.S. Cl. ..................... 43/125; 222/188; 222/189.01
(58) Field of Search ........................ 43/125, 127, 131, 43/144; D11/131.1; 206/389, 403–405; 222/188, 189.01, 549

(56) References Cited

U.S. PATENT DOCUMENTS

| 1,913,571 A | | 6/1933 | Strongsen | |
| 1,963,501 A | | 6/1934 | Mitchell | |
| 2,765,579 A | | 10/1956 | Gordon | 43/127 |
| 3,704,539 A | * | 12/1972 | Alvarez | 43/131 |
| 3,778,924 A | | 12/1973 | Okui | 43/129 |
| 3,796,002 A | | 3/1974 | Katsuda | 43/125 |
| 4,126,958 A | | 11/1978 | Yokoyama | 43/127 |
| 4,765,090 A | | 8/1988 | Kuan et al. | 43/127 |
| 4,959,925 A | | 10/1990 | Nelson et al. | 43/125 |
| 5,357,709 A | | 10/1994 | Lin | 43/131 |
| 5,657,574 A | | 8/1997 | Kandathil et al. | 43/125 |
| 6,061,950 A | | 5/2000 | Carey et al. | 43/125 |
| 6,272,791 B1 | * | 8/2001 | Pleasants | 43/131 |

FOREIGN PATENT DOCUMENTS

| GB | 2276547 | 10/1994 | .......... A01N/25/18 |

OTHER PUBLICATIONS

Author unknown A Punks brand box side depicting a bendable tab holder for a mosquito coil. undated, admitted prior art, Date unknown.
Author Unknown, Date unknown A Pianchu brand mosquito coil holder (and schematic), undated, admitted prior art.

* cited by examiner

Primary Examiner—Charles T. Jordan
Assistant Examiner—Kimberly S. Smith

(57) ABSTRACT

Disclosed herein is a container for holding a burnable coil bearing an active ingredient, such as an insecticide, insect repellant, deodorizer, or fragrance. The container includes a base having a raised coil support for mounting the coil and a spiral recess or spirally arrayed support peaks which permit air circulation beneath the coil and inhibit premature snuffing. The coil is enclosed by a cover having a downwardly depending hold-down aligned with the coil support to prevent the coil from moving in the container. The cover also has openings allowing air to pass into the container and vapors to be released. The cover is rotatably mounted to the base so that the cover openings can be selectively opened and closed to allow controlled venting and snuffing of the coil.

16 Claims, 4 Drawing Sheets

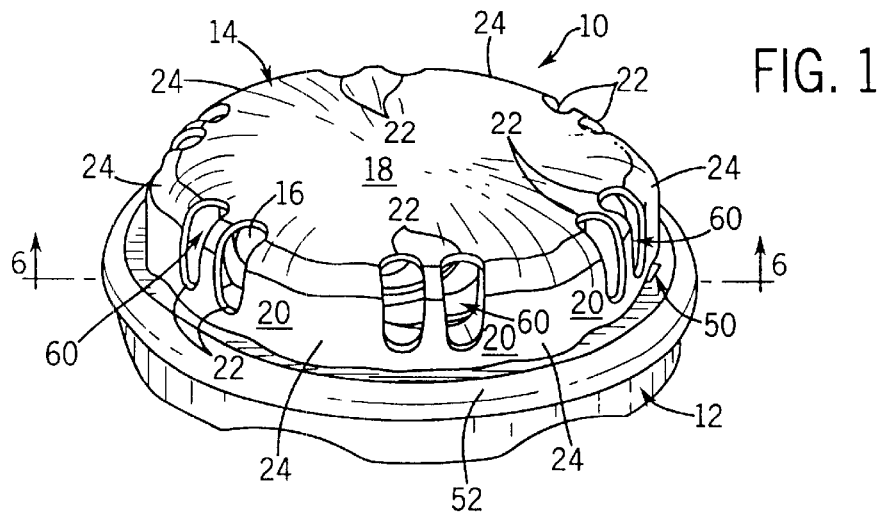

ADJUSTABLE BURNABLE COIL CONTAINER

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to containers for burnable coils, and in particular, to containers that provide adjustable burn rates and controlled snuffing.

Burnable coils, such as mosquito coils and incense coils, are designed to provide sustained vapor release. As they burn slowly they are susceptible to being inadvertently extinguished, thereby rendering the coil ineffective. Inadvertent extinguishing can occur when the coil does not receive enough air for burning, or when too much heat is drawn from the coil by conduction to a contacting surface.

Ordinarily, burnable coils are impaled on a spaded end of a post suitably mounted into the ground or a mounting surface. The coils are held off the ground/mounting surface and open to the air, thereby reducing the chance of inadvertent extinguishing. However, this leaves the burning end free to be touched. Moreover, the burn rate is largely affected by the rate of air flow past the coil. As such, a burning coil can be burned too quickly or extinguished by a strong wind.

Burnable coil holders have been developed in which the coils are enclosed inside a vented container. These containers shield the coil from excessive wind, are aesthetically pleasing and prevent accidental contact with the burning end of the coil. For example, U.S. Pat. No. 6,061,950 discloses a covered burnable coil holder in which the coil is mounted on a spade projecting from a base enclosed by a cover. The base has a number of small non-metallic pointed elements projecting upward to support the coil off the surface of the base (if it were to sag downwardly from the spade). The disclosure of this patent and of all other publications referred to herein are incorporated by reference as if fully set forth herein.

While a significant improvement, to extinguish a burning coil the cover had to be removed and the coil snuffed out directly. Further, if the holder was bumped accidentally, the coil might be jarred off the spade and snuffed.

Accordingly, a need still exists for an improved burnable coil holder.

BRIEF SUMMARY OF THE INVENTION

In one aspect the invention provides a container for a burnable coil having a base with a coil support for mounting the coil adjacent the coil's inward end. There is also a cover positioned on the base and having a downwardly depending hold-down alignable with the coil support. The cover also has openings for permitting the passage of air into the container. The term "cover opening" is defined to include both upwardly and sidewardly presented openings, as well as arrangements wherein space is purposefully left at the cover's margin, where the cover meets the base. The floor of the base and the hold-down sandwich the coil to prevent its movement during the burning process.

In preferred forms the coil support includes an upwardly extending projection, and the cover includes a downwardly extending leg having at least one foot. The base has at least one arc-shaped slot with an enlarged area through which the foot can readily pass and a narrow area through which the foot cannot readily pass. The arc-shaped slot is positioned to allow the cover to be rotated so that, as the leg is moved toward a first end of the slot, the openings are increasingly closed and, as the leg is moved toward the opposite end of the slot, the opening is increasingly opened. Preferably, when the leg is adjacent a first end of the slot the openings are essentially completely closed and when the leg is adjacent an opposite end of the slot the opening is essentially fully opened.

The base includes a ring of upstanding tabs spaced apart by gaps, the tabs and a floor of the base defining a cavity for receiving the coil. The cover has a top surface with walls depending downwardly therefrom that are sized to fit around the ring of tabs and enclose the cavity. When the cover is fixed to the base it can rotate between a closed position in which the wall openings align with the tabs and an open position in which the wall openings at least partially align with the gaps between the tabs. This provides venting control for the container.

In another aspect a comfort contact area can be provided on the cover by outwardly bulging grip areas formed at junctions between the cover walls.

To minimize the likelihood of undesired snuffing the base can either have a spiral depression in an upper surface of a floor of the base (so that only extreme sag will lead to a contact of an outer portion of the coil with the floor) or an array of spirally disposed pointed peaks extending up from the floor of the base (to inhibit sagging without significant contact with the outer portion of the coil).

It is preferred that the cover is made of a thermoset plastic and the base is made of a thermoset plastic or a sand-filled resin. Further, it is preferred that the base has a concave bottom surface and the cover has a convex top surface. This permits the containers to be nested for compact storage and shipment.

In another aspect the invention provides a container for controlling burn rates of a burnable coil. There is a base having a coil support for mounting the coil on the base, and a cover having openings for permitting the passage of air into the container. The cover is rotatably mounted on the base so that the cover openings can be selectively opened and essentially closed by relative rotation of the cover relative to the base.

In still other forms, the invention provides a mosquito coil having an upper and a lower surface, and an opening extending between the surfaces adjacent its inward end. The opening has a Saturn-shaped cross section. "Saturn-shaped" is defined as describing a circle with a line extending from side to side, through its center, somewhat resembling the planet Saturn and its rings, with the rings viewed edge-on. Alternatively, there may be two openings extending between the surfaces adjacent the coil's inward end, each opening having a different cross sectional shape (e.g. circular and elongated or square).

Thus, the present invention provides a container for a burnable coil allowing the burn rate, and thereby vapor release rate, to be easily controlled without contacting the coil. This is accomplished by rotating the cover in either direction to cause the openings to be more or less obstructed by the base.

Grip areas on the cover allow for easy manipulation of the cover as well as insulate one's hands from the heat of the coil. Inadvertent snuffing is avoided by the raised coil support, as well as the raised peaks or depressed recesses.

The coil is firmly pinned in place against movement within the container, being held between the coil support and the downwardly depending hold-down, and the coil support also contains a portion that will insure snuffing of the coil before the hold-down feature is contacted by the burning coil, thus allowing the hold-down and the cover to be made of materials that cannot withstand the intimately applied heat of the burning zone of a burning coil.

Alternatively described, the container of the invention for a burnable coil includes a base having a coil support for mounting the coil. The container also has a cover rotatably positionable on the base, the cover having at least one cover opening for permitting the passage of air into the container, the cover and base being so constructed that a user can rotate the cover on the base to increasingly close and open the cover opening.

Alternatively, the invention may be described as a container for a burnable coil having a base and a cover positionable on the base to enclose the coil as it burns. The base has a coil support for mounting the coil adjacent an end of the coil. The coil support has an upper surface to receive a portion of the coil in directly contacting relation, the upper surface being sufficiently heat absorbing as to cause a burning coil contacting the upper surface to extinguish when the fire reaches the margin of the flat upper surface. It is not required that the upper surface be flat, although that is preferred so as to provide better thermal drain from the coil to encourage prompt extinguishment of the coil.

The foregoing and other advantages of the invention will appear from the following description. In that description reference is made to the accompanying drawings which form a part hereof and in which there is shown by way of illustration preferred embodiments of the invention. These embodiments do not represent the full scope of the invention. Thus, the claims should be looked to in order to judge the full scope of the invention.

BRIEF DESCRIPTION OF THE DRAWINGS

FIG. 1 is a perspective view of an adjustable container of the present invention with an insect coil disposed therein;

FIG. 2 is an exploded view of the container and insect coil of FIG. 1;

DETAILED DESCRIPTION OF THE PREFERRED EMBODIMENTS

Figure 3:
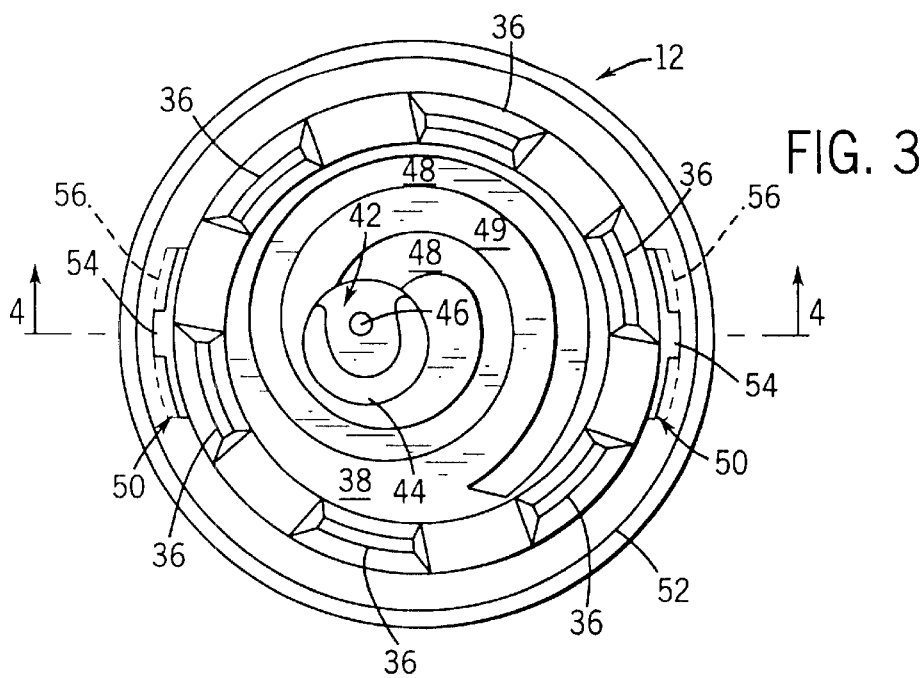
FIG. 3 is a top view of a base of the container of FIG. 1.

An adjustable insect coil container generally 10 includes a base 12 and a cover generally 14 that mate to enclose a burnable coil 16. The cover 14 has a generally hexagonal top surface 18 from which six side walls 20 depend downwardly. Each side wall 20 includes a pair of longitudinal vents 22, and the intersections of the side walls 20 present outwardly bulging six grip areas 24.

Figure 6:
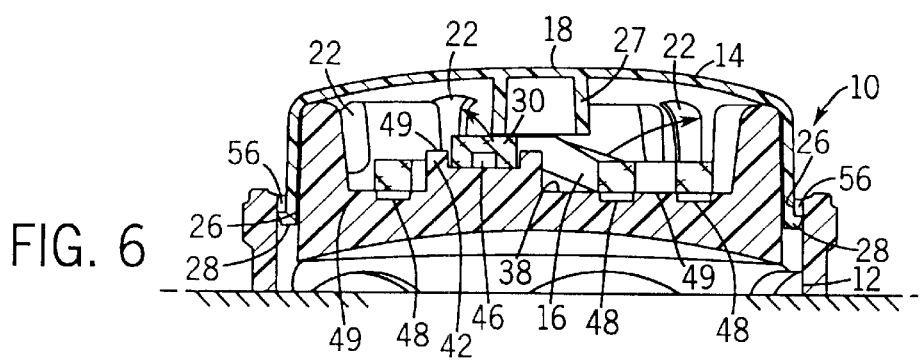
FIG. 6 is a vertical cross-sectional view taken along line 6—6 of FIG. 1.
Figure 7:
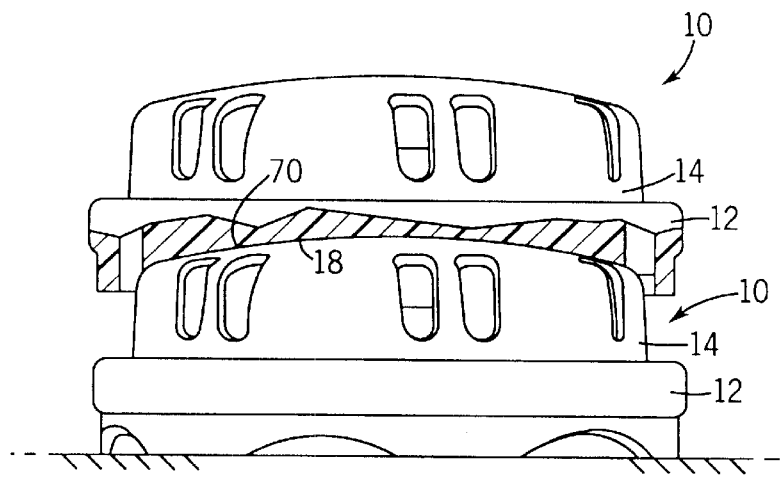
FIG. 7 is a partial sectional, partial side elevational view, showing that the cover and base are nestable.
Figure 8:
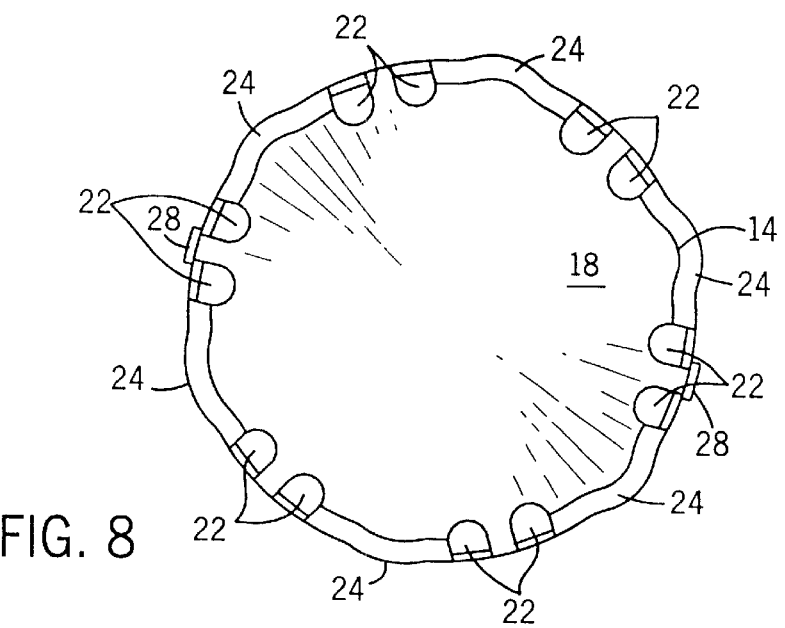
FIG. 8 is a top view of the cover.

Depending downwardly from the two opposite side walls are a pair of legs 26 having radially outwardly directed feet 28 at their bottom end. The legs 26 are designed to engage the base 12, as described in detail below. As shown in FIG. 6, the cover 14 also includes a downwardly depending coil hold-down 27, preferably tubular and located off-center of the cover 14. The hold-down may alternatively be a slab or other structure. The cover 14 is preferably made of a thermoset plastic having a sufficiently high melting point to sustain the heat of a burning coil without being damaged.

Preferably, the coil 16 has a mounting end 30 and an opposite burning end 32.

Figure 11A:
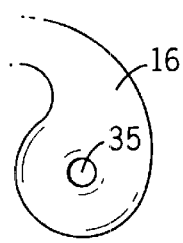
FIGS. 11A–11C show inner ends of insect coils with various through openings.
Figure 11B:
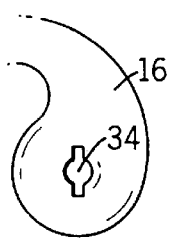

Referring to FIG. 11B, a Saturn-shaped opening 34 is formed in or through the mounting end 30 of the coil 16. This unique opening allows the coil 16 to be used with the container 10 of the present invention as well as with conventional spade-type holders and containers, such as that disclosed in U.S. Pat. No. 6,061,950. The coil 16 is otherwise of the type disclosed in U.S. Pat. No. 5,657,574.

Figure 11C:
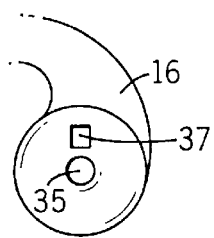

A variety of other spiral burnable coils could also be used that incorporate the desired materials to be dispersed (e.g. insecticides, insect repellants, deodorizers, fragrances and the like). Moreover, the mounting end 30 could have other mounting openings, such as a cylindrical through hole 35 as shown in FIG. 11A alone, or separate rectangular and circular openings 35 and 37 as shown in FIG. 11C.

The base 12 is preferably a sand-filled polymer resin or a suitable thermoset plastic formed to include six, equally-sized upstanding tabs 36 spaced apart from each other and arranged in a circle. The tabs 36, in conjunction with a bottom floor 38, define a cavity 40 in which the coil 16 can be disposed. The cavity 40 also acts to contain residual ash left over from a burnt coil 16.

Eccentrically located (to be in vertical alignment with the hold-down 27 of the cover 14) is a coil support 42 projecting upward from the floor 38. The coil support 42 has a horseshoe-shaped ridge 44, the inner diameter of which is designed to envelope the curved outer surface of the mounting end 30 of the coil 16. The coil support 42 also includes an upwardly projecting peg 46 which engages with the opening 34 in the mounting end 30 of the coil 16. The coil support 42 has a flat surface that can draw sufficient heat away from the contacting mounting end 30 of the coil 16 to snuff out a burning coil before reaching the ridge 44. Extinguishing the coil 16 before the mounting end 30 is burnt prevents the hold-down 27 of the cover 14 from coming in contact with a burning coil, which reduces the possibility of the cover being deformed.

The ridge 44 and peg 46 work to keep the mounting end 30 of the coil 16 on the coil support 42 elevated off of the floor 38. The floor 38 of the base 12 also has a spiral-shaped depression 48 designed to follow the spiral path of the coil 16. The recess 48 is slightly wider than the width of the coil 16. As such, a sagging coil will first fall into the recess in a manner that it is still above the floor. This makes heat loss to the base less likely. The spiral-shaped depression 48 also provides a vision reference for properly orienting and mounting the coil 16 within the base 12. By aligning the coil 16 with the depression 48 the user will be sure to mount the mounting end 30 of the coil 16 to the coil support 42.

Figures 5A, 5B, 5C:
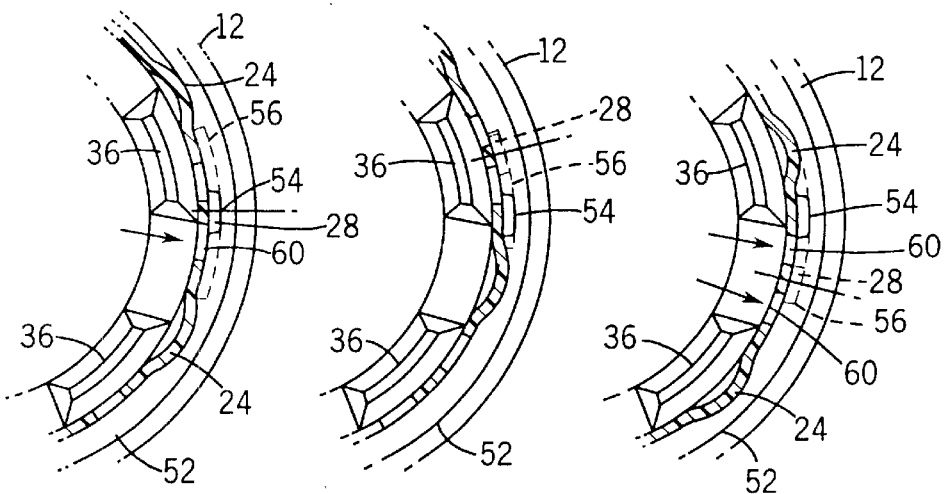
FIGS. 5A–5C are fragmentary views showing a cover of the container of FIG. 1 in various positions, FIG. 5A showing the cover positioned so that the vents are partially open, FIG. 5B showing the cover positioned so the vents are closed and FIG. 5C showing the cover positioned so the vents are fully open.

Referring now to FIGS. 2 and 3, the base 12 has a pair of arc-shaped slots 50 located opposite from each other in a circumferential flange 52 extending around the tabs 36. The slots 50 receive the legs 26 of the cover 14. The slots 50 have an enlarged opening area 54 through which the feet 28 initially can fit when attaching or removing the cover 14, as shown in FIG. 5A. When inserted into the slots 50, the legs 26 extend down far enough so that the feet 28 rest beneath a lip surface 56 of the base 12, as shown in FIG. 6. Thus, when the cover 14 is rotated, as in the positions shown in FIGS. 5B and 5C, the lip 56 prevents the cover 14 from being pulled away from the base 12.

As shown in FIG. 1, the base 12 and the cover 14 cooperate to form side air passages 60 allowing air to enter the container 10 and burnt vapors to exit during burning of the coil 16. The cover 14 can be rotated as desired to vary the degree that the vents 22 are obstructed. The base slots 50 are sized so as to positively stop the cover 14 in fully open and fully closed positions by contact with the legs 28 of the cover 14.

Thus, as shown in FIG. 5B, when the cover 14 is fully rotated counter-clockwise, the tabs 36 of the base essentially completely obstruct the vents 22 in the cover 14. In this way a burning coil can be snuffed without touching the coil by hand. Conversely, when the cover is fully rotated clockwise, the vents 22 align with air gaps between the tabs 36 and allow maximum air and vapor passage therethrough. Intermediate positions provide for intermediate bum rates.

Figure 4:
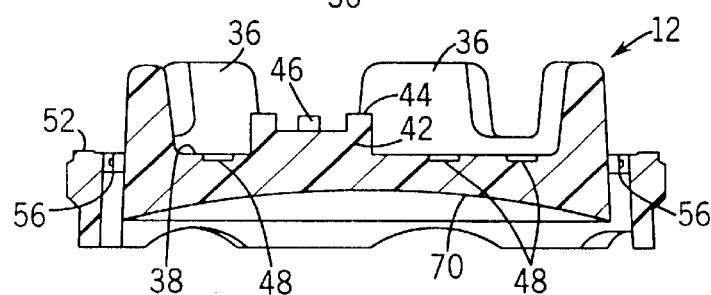
FIG. 4 is a cross-sectional view taken along line 4—4 of FIG. 3.

As shown in FIG. 4, the base 12 has a concave underside 70 that is shaped to mate with the convex top surface 18 of the cover 14. Multiple containers 10 can be compactly nested or stacked securely one upon another for storage or shipping.

The container 10 can be used, for example, to hold an insect coil containing a suitable insecticide active ingredient. As mentioned, however, the container 10 may also be used with other burnable coils having other types of active ingredients. In any event, the container 10 is preferably used by setting the base on a flat surface in an room or outdoor space. The coil 16 is then inserted into the base 12 so that the mounting end 30 of the coil is fit onto the coil support 42, with the peg 46 in the opening 34. Either before or after the coil 16 is placed in the base 12 the burning end 32 is lit with a match or lighter until the coil 16 begins burning. The cover 14 is then fit over the base 12 so that the legs 26 align with the slots 50 such that the feet 28 fit through the enlarged opening 54. The cover 14 can then be adjusted by grasping the grip areas 24 and rotating the cover 14 as needed to open the vents 22 so as to achieve a desired vapor release rate.

The cover 14 is preferably adjusted using the grip areas 24. This is because after prolonged burning portions of the cover 14 can become warm. The grip areas 24 lie farther outside the circumference of the tabs 36 than the vented area. As such, the grip areas 24 are cooler than other parts of the cover 14. The grip areas 24 are located at the corners of the side walls 20, which are natural grip points.

When the cover 14 is attached to the base 12 the coil is held against the coil support 42 by the hold-down 27, as shown in FIG. 6. If the container is accidentally tipped over, the coil 16 will remain burning without being extinguished.

Figure 9:
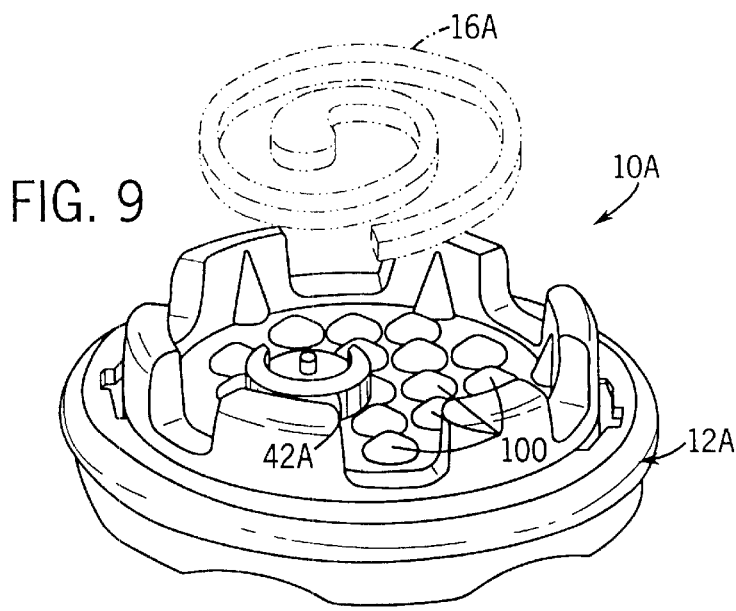
FIG. 9 is a perspective view of an alternate embodiment of the base in which the floor of the base has an array of raised spikes.
Figure 10:
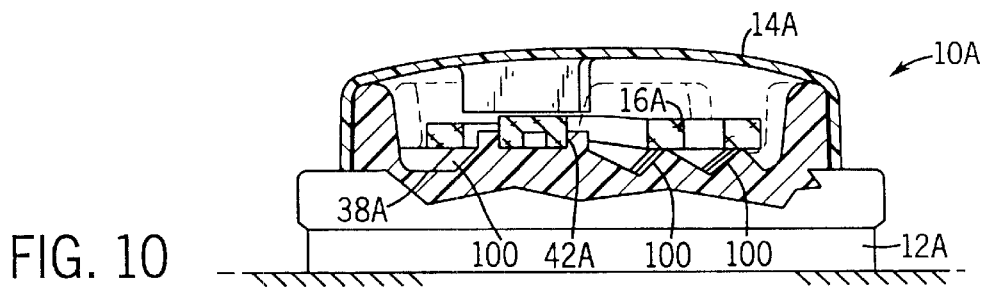
FIG. 10 is a view similar to FIG. 6, albeit with the base of FIG. 9.

Another embodiment of the container is shown in FIGS. 9 and 10 as reference numeral 10A. Similar components are shown with similar numbers, albeit with the suffix "A". As in the first embodiment, the container 10A includes a base 12A and a cover 14A for enclosing a coil 16A. The coil 16A is again supported above the floor 38A by a raised coil support 42A. However, here rather than a recess, the base 12A has a plurality of support peaks 100 around the coil support 42A for supporting the coil 16A in the event it sags downwardly. As with the recess in the first embodiment, the support peaks 100 allow air to pass beneath the coil 16A. Preferably, the support peaks 100 have a conical or pyramidal shape, terminating upwardly to a point so that they make as little point contact with the coil 16A as possible. The coil support 42A extends higher than the support peaks 100.

While specific embodiments have been shown, various modifications falling within the breadth and scope of the invention will be apparent to one skilled in the art. For example, the container of the first embodiment could include both a recess as well as the support peaks of the second embodiments. Also, while the container has been described with two identical cover legs and corresponding base slots, these features could be of different size or shape so that the cover can be fit on the base in only one orientation. Also, the cover could include any number of legs and be made to rotate in any direction to open and close the vents. Moreover, the configuration the cover, coil support ridge and the upstanding tabs of the base could be any suitable shape. Thus, the following claims should be looked to in order to understand the full scope of the invention.

Industrial Applicability

The above disclosed invention provides a container and snuffer for a burnable coil.

What is claimed is:

1. A container for a burnable coil, comprising:
   a base having a lower wall and a coil support extending up from the lower wall for mounting the coil adjacent an inward end of the coil; and
   a cover having an upper wall, the cover being positionable on the base and having a downwardly depending hold-down extendable down from the cover upper wall to be positionable adjacent the inward end of the coil while not adjacent to a burnable outer end of the coil and alignable with the coil support, the cover also having openings for permitting the passage of air into the container.

2. The container of claim 1, wherein the coil support includes an upwardly extending projection.

3. The container of claim 1, wherein the cover includes a downwardly extending leg having a foot, and wherein the base includes a slot having an enlarged area through which the foot can readily pass and a narrow area through which the foot cannot readily pass.

4. The container of claim 3, wherein the slot is positioned to allow the cover to be rotated so that when the leg is moved toward a first end of the slot the at least one cover opening is increasingly closed and when the leg is moved toward an opposite end of the slot the at least one cover opening is increasingly opened.

5. The container of claim 4 including more than one cover opening:
   wherein the base includes a ring of upstanding tabs spaced apart by gaps, the tabs and a floor of the base defining a cavity for receiving the coil;
   wherein the cover has a top surface with walls depending downwardly therefrom that are sized to fit around the ring of tabs and enclose the cavity; and
   wherein, the cover openings are located between the cover walls and, when the cover is mounted on the base, it can rotate between a closed position in which the cover openings align with the tabs and an open position in which the cover openings at least partially align with the gaps between the tabs.

6. The container of claim 3, wherein the slot is positioned to allow the cover to be rotated so that when the leg is adjacent a first end of the slot the at least one cover opening is essentially completely closed and when the leg is adjacent an opposite end of the slot the at least one cover opening is essentially filly opened.

7. The container of claim 6, wherein the cover has side cover walls and outwardly bulging grip areas are formed at junctions between the side cover walls.

8. The container of claim 1, wherein the base also includes pointed peaks extending up from the floor of the base.

9. The container of claim 1, wherein the cover is made of a heat tolerant plastic and the base is made of a material selected from the group consisting of a sand-filled resin, a heat tolerant plastic and combinations thereof.

10. The container of claim 1, wherein the base has a concave bottom surface opening away from the cover and the cover has a convex top surface.

11. The container of claim 1, wherein the coil support has a flat upper surface having a raised ridge along at least a portion of its perimeter.

12. A container for a burnable coil, comprising:
- a base having a coil support for mounting a burnable coil adjacent the coil's inward end; and
- a cover positionable on the base and having a downwardly depending hold-down alignable with the coil support, the cover also having openings for permitting the passage of air into the container;
- wherein the base further comprises a spiral depression in an upper surface of a floor of the base.

13. A container for a burnable coil, comprising:
- a base having a coil support for mounting a burnable coil adjacent the coil's inward end; and
- a cover positionable on the base and having a downwardly depending hold-down alignable with the coil support, the cover also having openings for permitting the passage of air into the container;
- wherein the coil support has a flat upper surface to receive a portion of a coil when the coil is supported thereon in directly contacting relation, the flat upper surface being sufficiently heat absorbing as to cause a burning coil supported thereon to extinguish when the fire reaches a margin of the flat upper surface.

14. A container for controlling burn rates of a burnable coil, comprising:
- a base having a lower wall and a coil support extending up from the lower wall for mounting the coil adjacent an inward end of the coil while the coil support is not in contact with a burnable outer end of the coil; and
- a cover positionable on the base and having openings for permitting the passage of air into the container, the cover being rotatably mounted on the base so that the cover openings can be selectively opened and essentially closed by rotation of the cover relative to the base.

15. A container for a burnable coil, comprising:
- a base having a lower wall and a coil support extending up from the lower wall for mounting the coil adjacent an inward end of the coil while the coil support is not in contact with a burnable outer end of the coil; and
- a cover rotatably positionable on the base, the cover having at least one cover opening for permitting the passage of air into the container, the cover and base being so constructed that a user can rotate the cover on the base to increasingly close and open the cover opening.

16. A container for a burnable coil, comprising a base and a cover positionable on the base to enclose a burnable coil as it burns, the base having a coil support for mounting the coil adjacent an end of the coil, the coil support having an upper surface to receive a portion of the coil in directly contacting relation, the upper surface being sufficiently heat absorbing as to cause a burning coil contacting the upper surface to extinguish when the fire reaches a margin of the upper surface.

* * * * *